United States Patent [19]

Paltauf et al.

[11] Patent Number: 5,665,714

[45] Date of Patent: Sep. 9, 1997

[54] N-SUBSTITUTED GLYCEROPHOSPHOETHANOLAMINES

[75] Inventors: Friedrich Paltauf; Albin Hermetter, both of Graz; Rudolf Franzmair, Linz, all of Austria

[73] Assignee: Clarion Pharmaceuticals Inc., Madison, Wis.

[21] Appl. No.: 758,934

[22] Filed: Dec. 3, 1996

Related U.S. Application Data

[60] Provisional application No. 60/008,350 Dec. 7, 1995.

[51] Int. Cl.$^6$ .................. A61K 31/415; C07D 233/16; C07D 403/04
[52] U.S. Cl. ........................................... 514/94; 548/119
[58] Field of Search ........................ 514/94; 548/119

[56] References Cited

U.S. PATENT DOCUMENTS

| | | | |
|---|---|---|---|
| 4,372,949 | 2/1983 | Kodama et al. | 424/199 |
| 4,650,791 | 3/1987 | Nomura et al. | 514/82 |
| 5,116,992 | 5/1992 | Braquet et al. | 514/77 |

OTHER PUBLICATIONS

Andreesen, R., "Ether Lipids in the Therapy of Cancer," *Prog. Biochem. Pharmacol.*, vol. 22, pp. 118–131 (Kaeger, Basal 1988).

Brachwitz et al, *Chemistry and Physics of Lipids*, vol. 31, pp. 33–52 (1982).

*Cell*, vol. 15, pp. 261–267 (1978).

Hermetter, A. and Paltauf, F., Procedures for the Synthesis of Ether Lipids, in H.K. Mangold and F. Paltauf, *Ether Lipids*, Academic Press (1983), p. 393 et.seq.

*J. Immunology*, vol. 119, pp. 950–954 (1977).

Paltauf, F. and Hermetter, A., *Methods Enzymol.*, vol. 197, pp. 134–149 (1991).

Paltauf, F., *Chem. Phys. Lipids*, vol. 74, pp. 101–139 (1994).

Trush et al., "The Generation of Chemiluminescence by Phagocytic Cells," *Methods in Enzymology* (1978), 57:462–494.

*Primary Examiner*—Joseph McKane
*Attorney, Agent, or Firm*—DeWitt Ross & Stevens S.C.

[57] ABSTRACT

The present invention relates to novel, therapeutically active fatty alkyl and alkenyl ether glycerophospholipids bearing a 3-(2-imidazolinyl)-2-imidazolinyl or 2-imidazolinyl substituent on the ethanolamine nitrogen, methods of using the compounds and pharmaceutically acceptable salts thereof, and pharmaceutical compositions containing same. The novel, therapeutically active compounds and salts of the invention possess anti-tumor, anti-psoriatic, anti-inflammatory, and anti-asthma activities.

30 Claims, 5 Drawing Sheets

N-SUBSTITUTED GLYCEROPHOSPHOETHANOLAMINES

This application claims priority to provisional application Ser. No. 60/008,350, filed Dec. 7, 1995.

FIELD OF THE INVENTION

The present invention relates to novel, therapeutically active fatty alkyl and alkenyl ether glycerophospholipids bearing a 3-(2-imidazolinyl)-2-imidazolinyl or 2-imidazolinyl substituent on the ethanolamine nitrogen, pharmaceutically acceptable salts of these compounds, methods of using these compounds and salts, and pharmaceutical compositions containing same. The compounds and salts of the invention have been discovered to possess anti-tumor, anti-psoriatic, anti-inflammatory, and anti-asthma activities.

BACKGROUND OF THE INVENTION

Synthetic fatty alkyl and alkenyl ether glycerophospholipids with potential anti-tumor properties have been reported in the literature. See, for example, F. Paltauf, Chem. Phys. Lipids 74, 101–139 (1994). The compound 1-O-octadecyl-2-O-methyl-sn-glycero-3-phosphocholine (ET 18-OCH$_3$) has markedly potent anti-tumor activity. See R. Andreesen, "Ether Lipids in the Therapy of Cancer," Prog. Biochem. Pharmacol. 22, 118–131 (Karger, Basel 1988). Treatment of cancer with a fatty alkyl ether glycerophosphoethanolamine component is also disclosed in U.S. Pat. No. 4,372,949. Halo substituted cytostatic analogs are described by H. Brachwitz et al., Chemistry and Physics of Lipids 31, 33–52 (1982). Glycerophospholipids bearing a C$_{10-24}$ alkyl ether substituent in the 1-position, a cyclic amido group in the 2-position, and a cyclic ammonio group as part of the phosphoethanolamino function in the 3-position of the glyceryl backbone are described in U.S. Pat. No. 4,650,791. Also disclosed in Pat. No. 4,650,791 are synthetic intermediates wherein the substituents are as described in the preceding sentence herein except that there is an hydroxyl group at the 3-position or hydroxyl groups at both the 1-position and the 3-position of the glyceryl backbone. Glycerophosphoethanolamines bearing a non-cyclic, substituted amino substituent in the 2-position and a lower C$_{1-5}$ alkyl ether substituent in the 1-position of the glyceryl backbone are disclosed in U.S. Pat. No. 5,116,992.

Applicants disclose for the first time herein that the novel fatty alkyl and alkenyl ether glycerophosphoethanolamines of the invention, which bear a 3-(2-imidazolinyl)-2-imidazolinyl or 2-imidazolinyl substituent on the ethanolamine nitrogen, and the pharmaceutically acceptable salts thereof, also possess anti-tumor-activity. Surprisingly, in addition, these novel fatty alkyl and alkenyl ether glycerophosphoethanolamines and salts have been discovered to also possess anti-psoriatic, anti-inflammatory, and anti-asthma activities.

The novel compounds and salts of the invention are also useful for treatment and prophylaxis of viral infections, as disclosed in the commonly owned, co-pending U.S. patent application filed on the same day as this Application, having the Title "Method for Treating Viral Infection" and Attorney Docket No. 43549/204. This commonly owned, co-pending Application is incorporated herein by reference in its entirety.

SUMMARY OF THE INVENTION

The invention provides novel fatty alkyl and alkenyl ether glycerophosphoethanolamines bearing a 3-(2-imidazolinyl) -2-imidazolinyl or 2-imidazolinyl substituent on the ethanolamine nitrogen and pharmaceutically acceptable salts of these compounds. The invention further provides a method of treating a tumor in a mammal with such which comprises administering to the mammal an anti-tumor effective amount of said glycerophosphoethanolamines or pharmaceutically acceptable salts thereof. The invention further comprises a method of treating psoriasis which comprises administering to a mammal suffering therefrom anti-psoriatic effective amounts of said glycerophosphoethanolamines of the invention or pharmaceutically acceptable salts thereof. The invention further provides a method of treating inflammation which comprises administering to a mammal suffering therefrom an anti-inflammatory effective amount of said glycerophosphoethanolamines of the invention or pharmaceutically acceptable salts thereof. The invention further provides a method of treating a disease, such as asthma, associated with PAF which comprises administering to a mammal suffering therefrom a PAF-activity-inhibiting-effective amount of said glycerophosphoethanolamines of the invention or pharmaceutically acceptable salts thereof. The invention further provides a pharmaceutical composition comprising an anti-tumor, anti-psoriatic, anti-inflammatory, or anti-PAF-activity effective amount of said glycerophosphoethanolamines of the invention or pharmaceutically acceptable salts thereof together with a pharmaceutically acceptable carrier.

DETAILED DESCRIPTION OF THE INVENTION

Figure 1:
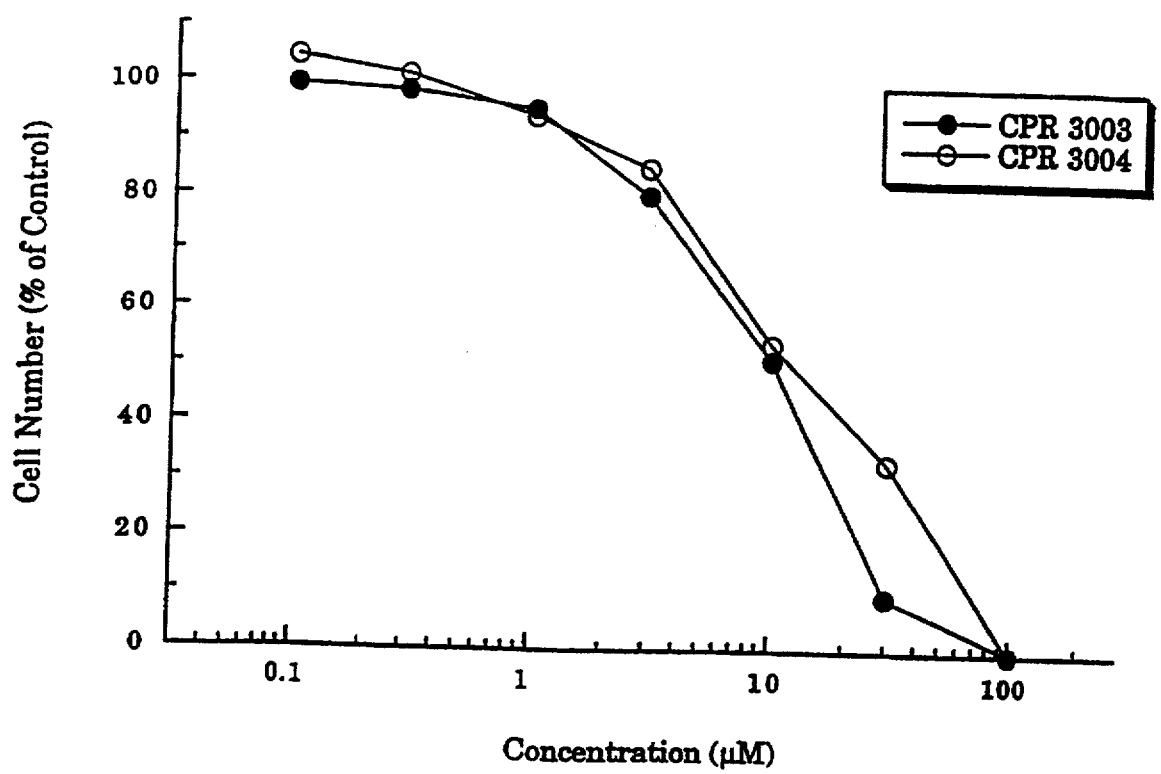
FIG. 1 is a graphical representation of results from an in vitro MDA-MB-231 cell inhibition assay of two compounds of the invention, designated CPR 3003 and CPR 3004.

The present invention relates to novel fatty alkyl and alkenyl ether glycerophospholipids, also referred to as fatty alkyl and alkenyl ether glycerophosphoethanolamines, which bear a 2-imidazolinyl substituent on the ethanolamine nitrogen. The subject compounds are represented by the general formula (I):

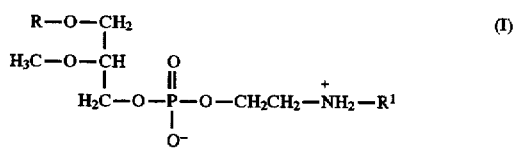

wherein R represents a substituted or unsubstituted straight or branched chain C$_{14-20}$ alkyl or alkenyl, said substituent being one or more of halo, C$_{1-3}$ alkoxy or cyano, provided that a double bond of said alkenyl does not involve the carbon atom of said alkenyl that is bonded to the oxygen of the glyceryl backbone; and $R^1$ is 3-(2-imidazolinyl)-2-imidazolinyl or 2-imidazolinyl.

The invention encompasses all optical and geometric isomers of the compounds of general formula (I) as well as salts of the formula (I) compounds and of said isomeric forms thereof.

The subject compounds wherein $R^1$ is 3-(2-imidazolinyl)-2-imidazolinyl are represented by formula (Ia):

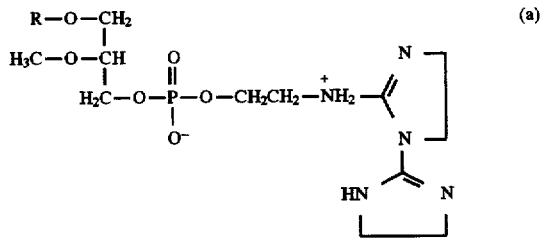

The subject compounds wherein $R^1$ is 2-imidazolinyl are represented by formula (Ib):

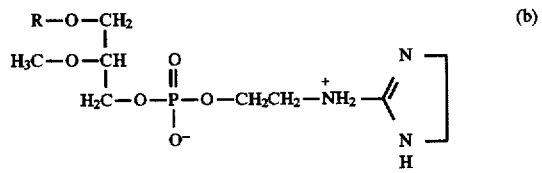

As used herein, R is selected from the group consisting of (1) substituted or unsubstituted, preferably unsubstituted, $C_{14-20}$ alkyl groups, preferably $C_{16-18}$ alkyl, such as, for example, tetra-, penta-, hexa-, hepta-, octa-, nonadecyl-, eicosyl-, or the branched analogs thereof; and (2) substituted or unsubstituted, preferably unsubstituted, $C_{14-20}$ alkenyl groups, preferably $C_{16-18}$ alkenyl, whereby a double bond of the alkenyl group does not involve the carbon atom of said alkenyl that is bonded to the oxygen of the glyceryl backbone. Both the aforementioned alkyl and alkenyl groups can be substituted at one or more carbons, preferably at one, with substituents which do not interfere with syntheses of the compounds during the synthetic steps of making them. Preferred substituents are halo, $C_{1-3}$ alkoxy or cyano. The term "halo" refers to any of the four halogens, chloro, bromo, iodo and fluoro, with chloro and fluoro being preferred.

The preferred Formula (I) compounds are the following:

1-O-n-octadecyl-2-O-methyl-glycero-3-phospho-N-[3-(2-imidazolinyl)-2-imidazolinyl]-ethanolamine, also referred to as CPR-3003;

1-O-n-octadecyl-2-O-methyl-glycero-3-phospho-N-(2-imidazolinyl)-ethanolamine, also referred to as CPR-3004;

1-O-n-hexadecyl-2-O-methyl-glycero-3-phospho-N-[3-(2-imidazolinyl)-2-imidazolinyl]-ethanolamine; and 1-O-n-hexadecyl-2-O-methyl-glycero-3-phospho-N-(2-imidazolinyl)-ethanolamine.

Other particular compounds of formula (I) are those wherein R is n-tetradecyl, n-eicosyl, 9-hexadecenyl, 9-octadecenyl, 2-chloro-n-octadecyl, 2-methoxy-n-octahexyl, 2-cyano-n-hexadecyl, cis- or trans-9-octadecenyl and cis- or trans-9-hexadecenyl.

I. CHEMISTRY

The compounds of the present invention may be prepared by the stepwise procedures outlined in the following reaction scheme, wherein Tr is triphenylmethyl (trityl) and Me is methyl, and the subsequent examples. The compounds produced by the reaction scheme may be purified by conventional methods of the art, e.g., chromatography, recrystallization, etc.

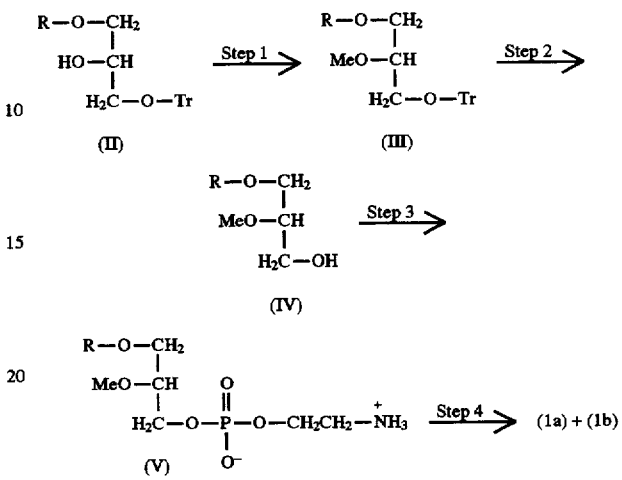

Step 1:

The compounds of Formula (II) are known in the literature or can be obtained by art-recognized procedures. See, for example, A. Hermetter and F. Paltauf, Procedures for the Synthesis of Ether Lipids, p. 393 et.seq., in H. K. Mangold and F. Paltauf, "Ether Lipids", Academic Press, 1983, and F. Paltauf and A. Hermetter, Methods Enzymol. 197, 134–149 (1991). Also see Examples 1–3 which follow. Treatment of (II) under an inert atmosphere with potassium t-butylate and dimethylsulfate in an inert aprotic solvent such as toluene at elevated temperatures yields the corresponding 2-methoxy compound, 1-O-R-2-O-methyl-3-O-trityl-glycerol (III), also known as methyl-trityl-batylalcohol when R=n-octadecyl.

Step 2:

Removal of the trityl function in compound (III) to yield 1-O-R-2-O-methyl-glycerol (IV), also known as methyl-batylalcohol when R=n-octadecyl, is readily accomplished by art-recognized procedures, e.g., by reacting a cooled solution (15°–18° C.) of Compound (III) in an inert aprotic solvent such as n-hexane with gaseous HCl.

Step 3:

The phosphoethanolamine moiety is introduced by reaction of the hydroxyl in Compound (IV) with $POCl_3$ and triethylamine at low temperatures (0°–4° C.) in an anhydrous solvent such as tetrahydrofuran, followed by reaction with ethanolamine, and treatment with aqueous dilute hydrochloric acid, to yield 1-O-R-2-O-methyl-glycero-3-phosphoethanolamine (V).

Step 4:

To a suspension of Compound (V) in an appropriate organic solvent, e.g., isopropanol, S-methyl-N,N'-ethyleneisothiourea is added and the mixture refluxed for several hours. After cooling to room temperature, the solvent is evaporated off. Water is added and the pH adjusted to about 4 with HCl solution. Conventional workup affords approximately equal amounts of the corresponding 3-(2-imidazolinyl)-2-imidazolinyl (I-a) and 2-imidazolinyl (I-b) compounds which are readily separated by conventional chromatographic techniques.

Working up the individual stepwise products indicated in the reaction scheme is advantageously carried out by standard methodologies, for example, by evaporating solvent from the reaction solution or precipitating the product from the reaction solution by dilution of the solution with an appropriate antisolvent (a solvent in which the product is less soluble than in the solvent of the reaction solution). The crude intermediate products obtained may be quite suitable, without further purification operations, for the preparation of the final products, which then may be purified. Particularly suitable methods for purifying the Formula I compounds are the conventional chromatographic methods, such as preparative thin-layer chromatography (TLC), column chromatography, adsorption chromatography, medium pressure liquid chromatography (MPLC) or high pressure liquid chromatography (HPLC).

The Formula I compounds have an asymmetric carbon atom (C2 position in the glyceryl backbone) in their structures. Consequently these compounds may exist in the form of different R and S optically isomeric forms (enantiomers) or racemates. Substantially pure forms of either of the R- and S-isomer may be obtained, substantially free of the other, by the application of art-known resolution methodologies such as, for example, column chromatography using chiral columns, starting the preparation from the R- or S-isomer of an appropriate precursor, for example, the starting Compound (II) shown in the reaction scheme.

In addition, cis- and trans-geometric isomers may also be present in the subject compounds, e.g., when R in Formula I is $C_{14-20}$ alkenyl, due to the cis- and trans-configuration inherent with the double bond. Thus, by initially starting with an appropriate cis- or trans-precursor, the corresponding end product of the Formula I compound will be obtained.

All isomeric forms of the Formula I compounds, including pure enantiomeric and geometric isomers and mixtures thereof, are intended to be within the scope of this invention. Unless otherwise specified, the compounds of the following examples are in racemic form.

The invention also comprehends salts of the Formula I compounds. These salts include acid addition salts, such as, for example, those made with hydrochloric, hydrobromic, nitric, sulfuric, phosphoric, carbonic, acetic, citric or lactic acids. The salts may also include those made with bases, such as, for example, sodium hydroxide, potassium hydroxide or calcium hydroxide. The salts of the invention are made by conventional methods well known to the skilled. The salts for therapeutic use of the Formula I compounds are pharmaceutically acceptable salts, as understood in the art.

II. UTILITY

The compounds of the subject invention and pharmaceutically acceptable salts thereof are useful chemopreventative and adjuvant agents in several aspects. They are useful for the treatment of cancerous tumors and also for treating inflammation, hyperproliferative skin diseases such as psoriasis, and asthma. The subject compounds and salts may be used alone for such indications or in combination with other compatible medicaments.

A. ANTI-TUMOR ACTIVITY

The anti-tumor activity of both naturally occurring and synthetic glycerol-derived ether lipids has been reported in the literature, for example, see R. Andreesen, "Ether Lipids in the Therapy of Cancer", Prog. Biochem. Pharmacol., vol.22, pp. 118–131 (Karger, Basel 1988).

The testing procedures described In Example 9 below, using human tumor cell lines in in vitro assays, demonstrate the marked anti-tumor (or antineoplastic or oncolytic) activity of the subject compounds and pharmaceutically acceptable salts thereof.

Anti-tumor activity is to be expected against a wide spectrum of mammalian (including human) tumors and cancerous growths such as cancers of the oral cavity and pharynx (lip, tongue, mouth, pharynx), esophagus, stomach, small intestine, large intestine, rectum, liver and biliary passages, pancreas, larynx, lung, bone, connective tissue, skin, colon, breast, cervix uteri, corpus endometrium, ovary, prostate, testes, bladder, kidney and other urinary tissues, eye, brain and central nervous system, thryoid and other endocrine glands, leukemias (lymphocytic, granulacytic, monocytic), Hodgkin's disease, non-Hodgkin's lymphomas, multiple myeloma, etc. Herein the terms "tumor", "cancer" and "cancerous growths" are used synonymously.

The disclosed invention thus provides a method of treating a tumor in a mammal. The treatment comprises administering to said mammal an anti-tumor effective amount of a compound of Formula (I) or a pharmaceutically acceptable salt thereof. The invention also provides pharmaceutical compositions comprising an anti-tumor effective amount of a formula (I) compound or a pharmaceutically acceptable salt thereof and a pharmaceutically acceptable carrier.

B. ANTI-PSORIASIS ACTIVITY

Psoriasis is a chronic inflammatory dermatosis characterized, in part, by hyperproliferation of keratinocytes and release of pro-inflammatory cytokines. Compounds that reduce hyperproliferation of keratinocytes in vitro are therefore likely to have utility in the control of psoriasis. As will be shown, using the assay described in Example 10 below, the subject compounds and pharmaceutically acceptable salts thereof markedly inhibit proliferation of these cells in vitro, thus indicating that these compounds and salts are useful in ameliorating psoriasis.

The instant invention thus provides a method of treating psoriasis in a mammal afflicted with same comprising administering to said mammal an effective anti-psoriatic amount of a compound of Formula I or a pharmaceutically acceptable salt thereof. It also provides pharmaceutical compositions comprising an effective anti-psoriatic amount of a compound of Formula I or a pharmaceutically acceptable salt thereof and a pharmaceutically acceptable carrier.

C. ANTI-INFLAMMATORY ACTIVITY

Inflammation is a complex process, involving a variety of cell types including macrophages. See, for example, S. L. Kunkel, "Inflammatory Cytokines", pp. 1–15, in Manual of Vascular Mediators, P. A. Ward, Editor, produced by the publishers of Hospital Practice. References relative to macrophages are numerous, including, for example, J. Immunology 119:950–954 (1977) and Cell 15: 261–267 (1978).

Macrophages are activated by infection and by a wide variety of non-infectious irritants and proinflammatory agents. Upon activation, macrophages participate in a variety of reactions. They may phagocytize bacteria and kill them by either oxygen-dependent or -independent pathways. With respect to the oxygen-dependent pathways, activation of macrophages induces them to increase oxygen consumption and produce reactive oxygen species (for example, radicals such as superoxide). Production of reactive oxygen species by activated macrophages is associated with inflammatory responses. In addition, on activation, macrophages release a variety of inflammatory cytokines, including several interleukins and tumor necrosis factor α (TNFα). Inhibition of any of these activation-related processes can lead to reduced inflammation.

For these reasons, macrophage activation is of critical importance in studies of the inflammatory process. Agents that reduce macrophage activation are likely to have utility as anti-inflammatories.

As will be shown, using the assay described in Example 11 below, the subject compounds and pharmaceutically acceptable salts thereof markedly reduce macrophage activation, thus indicating that these compounds and salts are useful in ameliorating inflammation.

The subject compounds are thus useful in the treatment of acute and chronic inflammatory diseases, such as, for example, dermatitis, conjunctivitis, bursitis, rheumatoid arthritis and the like.

The instant invention thus provides a method of treating inflammation in a mammal afflicted with same comprising administering to said mammal an effective anti-inflammatory amount of a compound of Formula I or a pharmaceutically acceptable salt thereof. It also provides pharmaceutical compositions comprising an effective anti-inflammatory amount of a compound of Formula I or a pharmaceutically acceptable salt thereof and a pharmaceutically acceptable carrier.

D. PAF ANTAGONISM

Platelet Activating Factor (PAF) has been shown to be a mediator of inflammation and has been found in lung fluids of asthma patients. PAF is a chemo-attractant and encourages the migration of neutrophiles and eosinophiles to sites of inflammation and to the airways of asthmatic patients. Moreover, PAF has been shown to be a powerful broncho constrictor of the airways of asthmatic patients. In addition, PAF has been found in the psoriatic lesions of psoriasis patients. Accordingly, antagonists of PAF have potential utility in treating inflammatory diseases, including rheumatoid arthritis, as well as asthma and psoriasis.

The discovery that the subject compounds and pharmaceutically acceptable salts thereof antagonize the activity of PAF, as demonstrated in Example 12 below, indicates that these compounds and salts are useful in treating inflammatory disease, including rheumatoid arthritis, as well as asthma and psoriasis. The instant invention thus provides a method of treating inflammatory diseases in a mammal, including rheumatoid arthritis, as well as a method of treating asthma and a method of treating psoriasis. These treatment methods comprise administering to said mammal an effective PAF antagonizing amount of a compound of Formula I or a pharmaceutically acceptable salt thereof. It also provides pharmaceutical compositions comprising an effective PAF antagonizing amount of a compound of Formula I or a pharmaceutically acceptable salt thereof and a pharmaceutically acceptable carrier.

Among the mammals that may be treated with the compounds, salts, therapeutic methods and formulations of the invention are, of course, humans.

III. FORMULATIONS

Formulations of the present invention, for medical use, comprise an active compound, i.e., a Formula I compound or a pharmaceutically acceptable salt thereof, together with an acceptable carrier for it and optionally other therapeutically active ingredients. The carrier must be pharmaceutically acceptable in the sense of being compatible with the other ingredients of the formulation and not deleterious to the recipient of it.

The formulations include those suitable for oral, rectal, parenteral (including subcutaneous, intramuscular and intravenous), nasal, or bronchial administration. Preferred formulations are those suitable for oral or parenteral administration. Topical formulations are also included, for, for example, anti-psoriatic usage.

It is noted that the Formula I compounds typically decompose on heating above about 200° C. This characteristic may need to be taken into consideration in, for example, preparing tablets on a commercial scale where the heat of compression may be a factor. The Formula I compounds are also rather insoluble in water and, accordingly, liquid formulations which account for this factor may be made according to art-recognized pharmaceutical techniques. Examples of these techniques include an injection wherein the active compound is dissolved in a suitable solvent or co-solvent such as an appropriate polyethylene glycol, or a propylene glycol or the like; a sealed gelatin capsule enclosing an oily solution of the active compound; a suppository of the active compound in a conventional suppository base such as cocoa butter; or a liposome formulation, for example, the active compound and a glycerophospholipid such as phosphatidylcholine. In any event, the aforementioned characteristics of the Formula I compounds are not uncommon in the pharmaceutical area and, accordingly, art-recognized pharmaceutical techniques are employed to prepare appropriate formulations for such compounds as those of formula I or pharmaceutically acceptable salts thereof.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid or solid carrier and then, if necessary, shaping the product into desired unit dosage form.

Formulations of the present invention suitable for oral administration may be presented as discrete units such as capsules, cachets, tablets, boluses or lozenges, each containing a predetermined amount of the active compound; as a powder or granules; or in liquid form, e.g., as suspension, solution, syrup, elixir, emulsion, dispersion, liposome preparation, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

Formulations suitable for parenteral administration conveniently comprise a sterile preparation of the active compound in, for example, a polyethylene glycol 200 or propylene glycol solution which is preferably isotonic with the blood of the recipient.

Useful formulations also comprise concentrated solutions or solids containing the compound of Formula I which upon dilution with an appropriate solvent give a solution suitable for parenteral administration.

Preparations for topical or local applications, which are, for example, conventional for anti-psoriatic usage and may be useful in treatment of certain cancers, comprise aerosol sprays, lotions, gels, ointments, transferosomes, plasters, etc. and pharmaceutically acceptable vehicles therefore such as, for example, lower aliphatic alcohols, polyols such as glycerol, polyethyleneglycerol, esters of fatty acids, oils and fats, silicones, and other conventional topical carriers, for example, liposomes.

In topical formulations, the compounds of Formula I are preferably utilized at concentrations of from about 0.1% to about 5.0% percent by weight.

In addition to the aforementioned ingredients, the formulations of this invention may further include one or more optional accessory ingredients(s) utilized in the art of pharmaceutical formulations, e.g., diluents, buffers, flavoring agents, binders, surface active agents, thickeners, lubricants, suspending agents, preservatives (including antioxidants) and the like.

The compounds of Formula I and salts thereof of the invention are to be administered under the guidance of a physician or veterinarian.

The amount of compound of Formula I or salt thereof required to be effective for each of the indicated activities will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound or salt to be administered. However, a suitable effective dose is in the range of about 0.1 to about 200 mg/kg body weight per day, preferably in the range of about 1 to about 100 mg/kg per day, calculated as the non-salt form of compound of Formula I. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

For example, for a 75 kg mammal, a dose range would be about 7.5 to about 1500 mg per day, and a typical dose would be about 800 mg per day. If discrete multiple doses are indicated, treatment might typically be 200 mg of a compound of Formula I given 4 times per day.

In general, the pharmaceutical compositions of this invention contain from about 0.5 mg to about 500 mg and, preferably, from about 5 to 350 mg of active ingredient (compound of Formula I per se or as part of a pharmaceutically acceptable salt), preferably in a unit dosage form, for each of the indicated activities of the invention.

The following examples are intended to illustrate and not to limit the scope of the present invention.

EXAMPLE 1

A. Octadecylmethanesulfonate

500 Grams (1.85 mol) of 1-octadecanol is suspended with stirring in 2500 ml methylene chloride and 224.5 g (2.22 mol; 310 ml) triethylamine is added with cooling (cold water). 254 Grams (2.215 mol; 171.5 ml) of methanesulfochloride dissolved in 500 ml methylene chloride is then added in such a way that the reaction temperature is maintained between 20° and 25° C. Stirring at ambient temperature is continued for 1.5 hours. The methylene chloride is removed under vacuum at a temperature of 35° C. maximum. To the remaining syrup 1000 ml of ethanol/water (1/1; v/v) are added and remaining methylene chloride is completely removed under vacuum. (Note: In the presence of even traces of methylene chloride, the product will not crystallize). An additional 2500 ml ethanol/water (1/1; v/v) is added with stirring. The resulting crystallizate is filtered off, washed three times with ethanol/water (1/1; v/v) and air-dried to yield 641 g (99.4%) of octadecylmethanesulfonate; m.p. 60°–61° C.; water content does not exceed 0.5%. B. By utilizing an equivalent amount of an appropriate $C_{14-20}$ alkanol or alkenol in the foregoing procedure, the following methanesulfonates are obtained:

n-tetradecylmethanesulfonate;
n-hexadecylmethanesulfonate;
n-eicosylmethanesulfonate;
cis-9-octadecenylmethanesulfonate;
trans-9-octadecenylmethanesulfonate;
cis-9-hexadecenylmethanesulfonate;
trans-9-hexadecenylmethanesulfonate;
2-chloro-n-octadecylmethanesulfonate;
2-methoxy-n-octadecylmethanesulfonate; and
2-cyano-n-hexadecylmethanesulfonate.

EXAMPLE 2

A. 1-O-n-Octadecyl-Glycerol (Batylalcohol)

In an argon atmosphere, 79.2 g (1.2 mol) powdered potassium hydroxide (purity 85%) is suspended in 1680 ml dimethylsulfoxide. 118.88 Grams (0.9 mol) solketal (rac-1, 2-isopropylidene-glycerol) is added and the mixture is stirred for one hour at ambient temperature (18°–23° C.). Stirring is continued and 209.16 g (0.6 mol) octadecylmethanesulfonate is added. Stirring is continued for another three hours and the reaction mixture is kept overnight at ambient temperature.

No argon atmosphere is necessary. A mixture of 840 ml methanol and 336 ml conc. HCl is added and the reaction mixture is refluxed with stirring for one hour. Stirring is continued for another two hours, followed by cooling the reaction mixture to 30° C. Then 1040 ml methanol is added and stirring is continued for 10 minutes. Upon keeping the reaction mixture at 4° C. overnight, a precipitate is formed which is filtered off and washed with 300 ml methanol/water (1:1; v/v) and 1000 ml water. The crude product is then suspended (without drying) in 6400 ml water and the suspension is vigorously stirred for 30 minutes. The precipitate is filtered off and washed with three portions of 500 ml water. The crystallizate is dried under vacuum over phosphorous pentoxide to yield 190 g (92%) of batylalcohol; m.p. 68°–70° C. B. By substituting an equivalent amount of each methanesulfonate of Example 1-B for the octadecylmethanesulfonate of Example 2-A, each corresponding 1-O-R-glycerol is obtained.

EXAMPLE 3

A. 1-O-n-Octadecyl-3-O-Trityl-Glycerol (Tritylbatylalcohol) (II)

51.69 Grams (150 mmol) of batylalcohol and 62.73 g (225 mmol) freshly recrystallized tritylchloride are dissolved at 35° C. in 350 ml methylene chloride. (Note: It is recommended that the tritylchloride be freshly recrystallized from halpasol, trademark for a petroleum ether fraction, b.p. 100°–120° C.). During 15 minutes, 22.77 g (225 mmol; 31.38 ml) triethylamine is added dropwise to the stirred solution at 30°–35° C. (cooling with a water bath). The reaction is continued for six hours at ambient temperature. (Note: It is recommended that a control TLC be done to make sure that the reaction is complete). The solution is then washed with 300 ml of a $NaHCO_3$ solution (1%), dried over anhydrous sodium sulfate, filtered and evaporated under vacuum. The oily residue (155 g) is dissolved in 660 ml acetonitrile by warming up to 70° C. with stirring. After cooling to room temperature the title product crystallizes (preferentially after adding a few seed crystals). Crystallization is completed by standing overnight at ambient temperature. The crystallizate is filtered off to yield 82.5 g (93.7%) of crude product (m.p. 53°–55° C.) which can be used for the following step without purification. Recrystallization from halpasol (310 ml) yields 71 g (80%) of pure tritylbatylalcohol. B. In a similar way, introduction of the 3-O-trityl function is accomplished for each 1-O-R-glycerol of Example 2-B.

EXAMPLE 4

1-O-n-Octadecyl-2-O-Methyl-3-O-Trityl-Glycerol (Methyl-Trityl-Batylalcohol) (III)

Under an inert atmosphere (argon or nitrogen), 586.0 g (1 mol) trityl-batylalcohol (III) and 112.2 g (1 mol) potassium-t-butylate are dissolved in 2000 ml toluene with stirring, heated to 85° C. and within 30 minutes 63.07 g (0.5 mol) dimethylsulfate (47.4 ml) are added. The temperature is raised to 100° C. and then the reaction mixture is refluxed for one hour. After cooling to 98° C., 112.1 g (1 mol) potassium-t-butylate and 63.07 g (0.5 mol) dimethylsulfate are added within 30 minutes while the mixture is refluxed. Refluxing with stirring is continued for 6 hours; then the mixture is kept overnight at room temperature. The mixture is extracted with water (3×2000 ml) and the organic layer is evaporated under vacuum to yield 620 g of the 1-O-n-octadecyl-2-O-methyl-3-O-trityl-glycerol (methyl-trityl-batylalcohol) as an oily residue, which can be used in the following detritylation step without purification.

TLC:KG 60 F (Merck);

Mobile Phase: $CH_2Cl_2$; Rf: 0.20; Rf of an impurity (<5%) 0.02;

Visualized by iodine; (more sensitive visualization is achieved with chromate-sulphuric acid).

Pure methyl-trityl-batylalcohol III can be obtained by MPLC:

Apparatus: Waters PREP 500;

2 Silica cartridges (equals approx. 800 g silica, normal phase);

Mobile Phase: $CH_2Cl_2$;

Sample: 15 g raw (III) dissolved in 30 ml $CH_2Cl_2$;

Axial Pressure: 38 bar;

Internal Pressure: 9–15 bar;

Flow Rate: 200 ml/min;

Detection: RI-detector; Split 1:100

EXAMPLE 5

1-O-n-Octadecyl-2-O-Methyl-Glycerol (Methyl-Batylalcohol) (IV)

616.3 Grams (calculated with impurities, 1 mol=600.9 G) of crude methyl-trityl-batylalcohol (III) from Example 4 is dissolved in 1350 ml n-hexane and cooled to 15°–18° C. Within two hours 44 g (1.21 mol) gaseous HCl is passed into the stirred solution at the same temperature. After 30 minutes, tritylchloride starts to precipitate. The mixture is stirred for an additional hour at 15°–18° C. The precipitate is filtered off and washed with 250 ml cooled (16° C.) n-hexane. After air-drying, 214 g (76.76%) tritylchloride are obtained. The hexane phases are combined and kept at –20° C. overnight. The crystallized product is filtered off and washed with 220 ml cold (–20° C.) n-hexane. After air-drying, 331.35 g (92.4%) crude methyl-batylalcohol (IV) are obtained. (Note: Depending on the amount of co-crystallizing trityl derivatives, the yield may exceed 100%. Another impurity is n-octadecanol which should be removed in any case because in the next reaction step it may form phospholipids that cannot be separated from the product.)

Purification: 500 Grams raw methyl-batylalcohol are dissolved in 1500 ml toluene and slowly filtered through a bed of 1500 g alumina on a glass frit. (Note: The alumina bed is prepared by filtering a slurry of alumina in toluene). The alumina is washed with 1500 ml toluene. The toluene phases are combined and evaporated to dryness under reduced pressure. Recrystallization from n-hexane at –20° C. yields 402.2 g methyl-batylalcohol (IV) of sufficient purity to be used in the next step.

TLC:KG 60F (Merck);

Mobile Phase: $CH_2Cl_2$/EtOAc (4/1, v/v);

Rf: 0.40;

Visualized by iodine or by chromate-sulphuric acid.

Purification of raw methyl-batylalcohol by MPLC:

Steel column: 50×500 mm, Amicon (Grace);

Matrex silica: 20–45µ, normal phase (Grace);

Mobile phase: $CH_2Cl_2$/EtOAc (22/3; v/v);

Sample: 20.7 g raw (IV) dissolved in 25 ml $CH_2Cl_2$;

Internal pressure: 8–12 bar;

Flow rate: 156 ml/min;

Detection: RI-detector or TLC;

Pure methyl-batylalcohol (IV): m.p. 43°–44° C.

EXAMPLE 6

1-O-n-Octadecyl-2-O-Methyl-Glycero-3-Phosphoethanolamine (V)

A mixture of 40 ml anhydrous tetrahydrofuran (THF) and 36.8 g $POCl_3$ (240 mmol) is cooled to 0° C. Into this stirred solution, a mixture of 72 g (200 mmol) methyl-batylalcohol (IV), 36.4 g (360 mmol) triethylamine and 240 ml THF is added dropwise as the temperature is maintained at 0°–4° C. Some material precipitates. The cooling device is removed and a mixture of 14.7 g (240 mmol) ethanolamine, 36.4 g (360 mmol) triethylamine and 180 ml THF is added to the stirred solution within 15 minutes. The temperature rises to about 55° C. and stirring is continued at this temperature for one hour. After cooling to 15° C., a mixture of 30 ml conc. HCl and 170 ml water is added at 25°–30° C. The reaction mixture is allowed to come to ambient temperature and stirring is continued for one hour. The water layer is removed and the THF layer is diluted with 600 ml methylenechloride. 50 grams of sodium bicarbonate are added with vigorous stirring. After continuing stirring for 15 minutes, anhydrous sodium sulfate is added and stirring is continued for a few minutes. The inorganic material is removed by filtration and the solvent is evaporated under reduced pressure. The honey-like residue is taken up in 500 ml methylene chloride and a slight turbidity is removed by adding charcoal followed by filtration over a glass filter. Half of the methylenechloride is distilled off and 200 ml acetone are added. Upon cooling to 0° C. for two hours, 91.2 g (94.7%) of raw product (V) precipitates. This material is dissolved in 800–900 ml boiling isopropanol. The solution is passed over a filter and cooled to room temperature. On standing overnight at room temperature 86.3 g (89.5%) of crystalline 1-O-n-octadecyl-2-O-methyl-glycero-3-phosphoethanolamine (V) is obtained.

TLC:KG 60 F (Merck);

Mobile phase 1: $CHCl_3/CH_3OH/c. NH_3$; 65/35/5 per vol.;
Rf: 0.22;

Mobile phase 2: $CHCl_3/CH_3OH/acOH/HOH$; 100/60/20/5 per vol.;
Rf: 0.18;

Visualized by chromate-sulphuric acid.

Purification of (V) by MPLC:
  Steel column: 50×500 mm, Amicon (Grace);
  Matrex silica: 20–45μ, normal phase (Grace);
  Sample: 30 g (V) dissolved in 100 ml $CH_2Cl_2$ and 20 ml $CH_3OH$;
  Internal pressure: 8–10 bar;
  Flow rate: 78–156 ml/min;
  Detection: RI-detector or TLC.

EXAMPLE 7

1-O-n-Octadecyl-2-O-Methyl-Glycero-3-Phospho-N-[3-(2-Imidazolinyl)-2-Imidazolinyl]-Ethanolamine (CPR 3003) and 1-O-n-Octadecyl-2-O-Methyl-Glycero-3-Phospho-N-(2-Imidazolinyl)-Ethanolamine (CPR 3004)

To a suspension of 9.63 g (20 mmol) of 1-O-n-octadecyl-2-O-methyl-glycero-3-phosphoethanolamine (V) in 300 ml isopropanol, 9.3 g (80 mmol) of S-methyl-N,N'-ethylene thiourea are added and the mixture is refluxed for six hours. After standing overnight at room temperature, the solvent is evaporated under vacuum. Water (150 ml) is added to the residue and the pH of the suspension is brought to 4 by addition of approximately 14 ml 4N HCl. The gelatinous suspension is extracted with two portions of chloroform-methanol (2:1, v/v) and the organic phase is dried over anhydrous sodium sulphate. The sodium sulphate is then filtered off and the solvent is removed under vacuum. The residue is stirred overnight with 150 ml diethylether. The solid product is filtered off and air-dried to yield 12 g of crude product consisting of approximately equal amounts of CPR 3003 and CPR 3004. The two compounds are separated and purified by MPLC, using 800 g silica gel as the stationary phase and $CH_2Cl_2/CH_3OH/HOH$ (40/15/1.5, v/v/v) as the mobile phase. The yield of pure CPR 3003 and CPR 3004 is on the order of 2.5 g each. The remainder is recovered as a mixture of both compounds which can be rechromatographed for further yields. If CPR 3004 is of primary interest, a 1.5-fold excess of S-methyl-N,N'-ethylene thiourea should be utilized instead of the indicated 4-fold excess.

EXAMPLE 8

By following the procedures outlined in examples 4–7, except that an equivalent amount of each 1-O-R-3-O-tritylglycerol of Example 3-B is employed as the starting material, the following respective end products of formula (I-a) and formula (I-b) are obtained: the corresponding 1-O-n-tetradecyl-, 1-O-n-hexadecyl-, 1-O-n-eicosyl-, 1-O-(9-octadecenyl)-, 1-O-(9-hexadecenyl)-, 1-O-(2-chloro-n-octadecyl)-, 1-O-(2-methoxy-n-octadecyl)- and 1-O-(2-cyano-n-hexadecyl)- derivatives of 2-O-methyl-glycero-3-phospho-N-[3-(2-imidazolinyl)-2-imidazolinyl]-ethanolamine (I-a) and 2-O-methyl-glycero-3-phospho-N-(2-imidazolinyl)-ethanolamine (I-b).

EXAMPLE 9

Assay for Anti-Tumor/Antineoplastic Activity

1. Human tumor cell lines, available from the American Type Culture Collection (ATCC):

a. MDA-MB-231 (ATCC HTB 26): an estrogen receptor negative human breast carcinoma cell line (attachment dependent); and b. HT-29 (ATCC HTB 38): a human colon carcinoma cell line (attachment dependent).

2. Culture media:

a. for cell line 1-a: Dulbecco's Modified Eagle's Medium (DMEM) plus 10% Fetal Bovine Serum (FBS); and b. for cell line 1-b: 1:1 DMEM and Ham's F-12 (DMEM/F12) plus 10% FBS.

3. Standard protocol for culturing cell lines: in T-75 or T-150 flasks; 37° C.; 95% air, 5% $CO_2$; 100% humidity.

a. Cell lines 1-a and 1-b are passaged when approximately 80% confluent; with trypsin (1 mg/mL) and EDTA (1 mM EDTA in Ca-Mg free Hank's balanced salt solution); at a 1:4 to 1:5 split.

b. All procedures are performed aseptically in a Class II biological safety cabinet using standard BL-2 containment procedures. At approximately monthly intervals, fresh cells are thawed from liquid nitrogen storage in order to prevent genetic drift in stock cell lines.

4. Assay Procedure:

a. After cell passage, count cells with a hemocytometer;

b. Adjust concentration to approximately 5,000 cells per 100 μL;

c. Pipette 100 μL cell suspension per well of a standard 96-well microtiter plate;

d. Preincubate 24 hours to allow cells to attach;

e. Add 100 μL of test compound dispersed in phosphate buffered saline (PBS) and diluted in DMEM (for MDA-MB-231 cells) or DMEM/F12 (for HT-29 cells) to achieve final concentration levels ranging from 0 to 100 μM; and f. Incubate 48 hours under standard culture conditions and determine end points.

5. End Point:

a. Remove media and add 100 μL/well of cold (4° C.) 10% (w/v) trichloroacetic acid (TCA) in water;

b. After 1 hour at 4° C., remove TCA and rinse cells 5 times with tap water;

c. Air-dry plates;

d. Add 50 μL/well of 0.4% (w/v) sulforhodamine B (SRB) in 1% (v/v) acetic acid in water;

e. After 30 minutes at room temperature, rinse cells 4 times with 1% (v/v) acetic acid in water to remove residual stain;

f. Air-dry plates;

g. Dissolve stain by adding 100 μL/well of unbuffered Tris base, pH 10.5;

h. Read absorbance at 564 nm using a standard 96-well microtiter plate reader. Absorbance readings are linear with dye concentrations below 1.8 absorbance units. To reduce absorbance, decrease wavelength at which measurements are taken.

Figure 2:
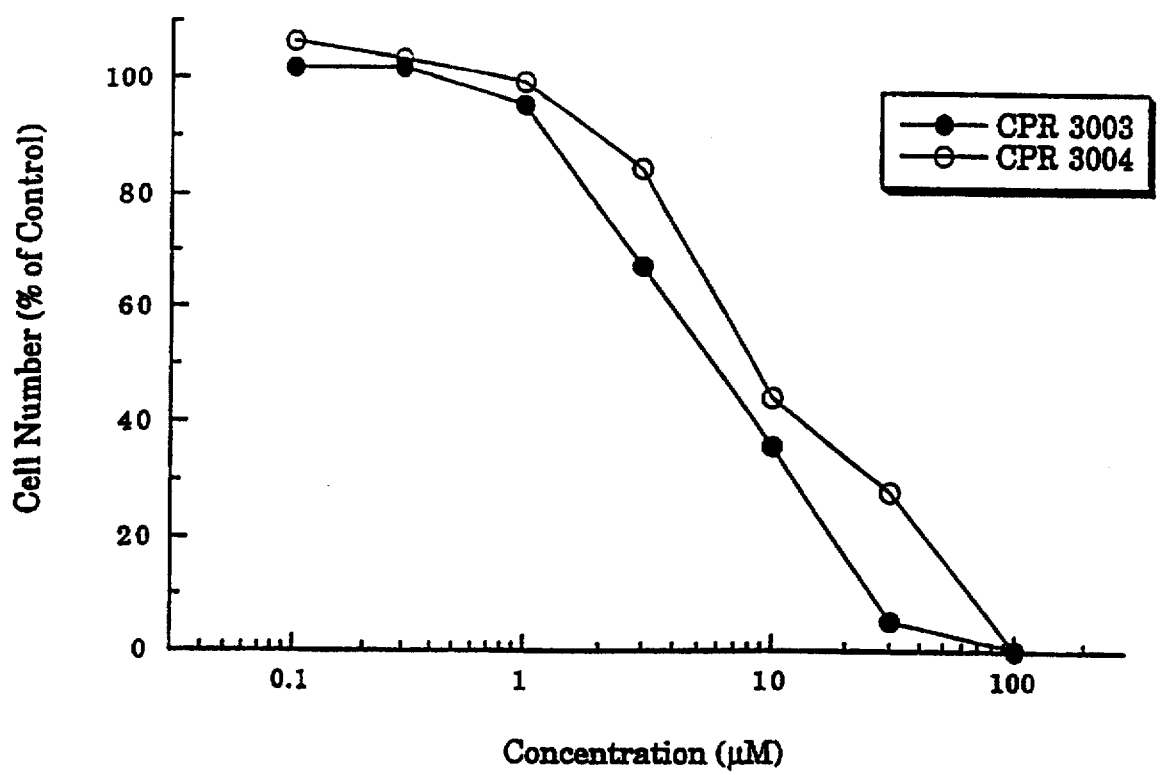
FIG. 2 is a graphical representation of results from an in vitro HT 29 cell inhibition assay of two compounds of the invention, designated CPR 3003 and CPR 3004.

6. Data Analysis:

a. For a single point reading, a higher absorbance indicates a higher cell number;

b. Control—no test compound present in culture medium;

c. Background—no cell and no test compound present in culture medium;

d. Calculate CN (cell number as % of Control):

$$CN = \frac{A(\text{test compound}) - A(\text{background})}{A(\text{control}) - A(\text{background})} \times 100$$

where A(test compound) is absorbance with test compound present in the culture medium, A(control) is absorbance of control, and A(background) is absorbance of background;

7. Results are represented in FIGS. 1 and 2, which illustrate the marked inhibition of cell growth at concentrations above 3 µM by the compounds tested (CPR 3003 and CPR 3004).

EXAMPLE 10

Assay for Anti-psoriatic Activity by Inhibition of Keratinocyte Proliferation

Figure 3:
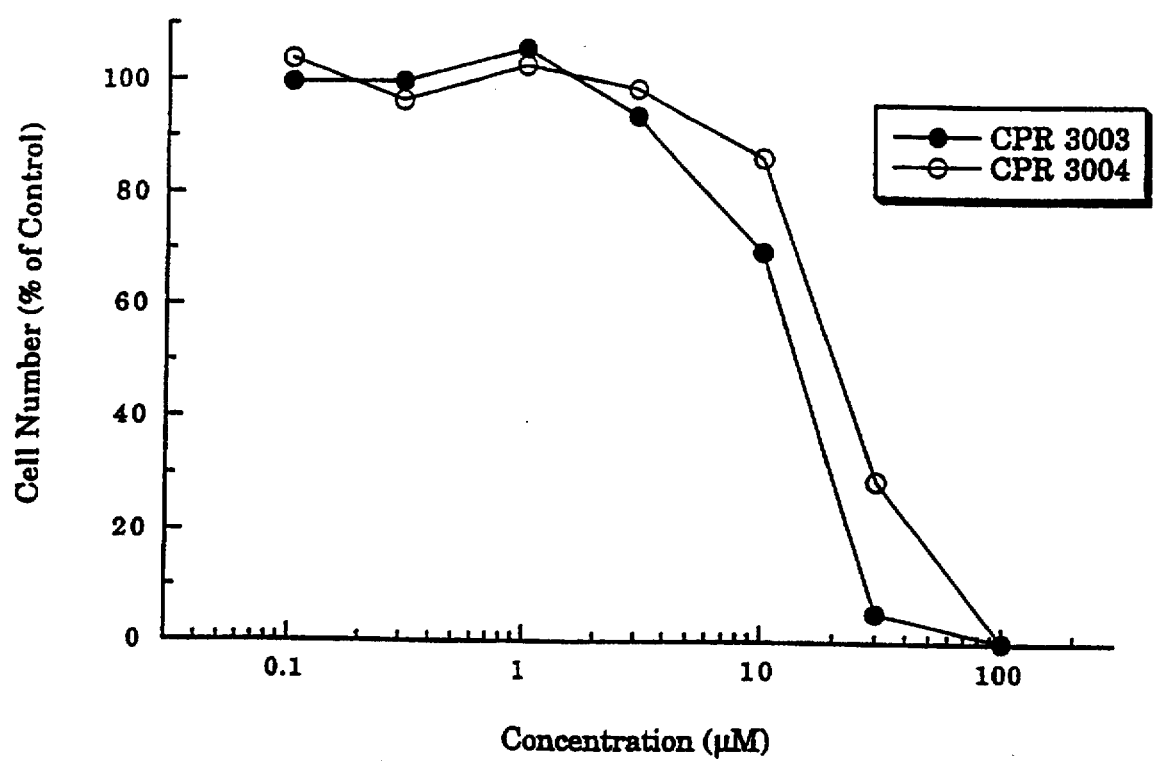
FIG. 3 is a graphical representation of results from an in vitro PAM-212 cell inhibition assay of two compounds of the invention, designated CPR 3003 and CPR 3004.

1. Cell line: PAM-212 murine keratinocyte cell line isolated and cultivated from newborn BALB/c mice (see S. H. Yuspa et al., Cancer Research, 40, 4694–4703, December, 1980) that appears to retain many characteristics of normal keratinocytes.
2. Culture medium: 1:1 DMEM and Ham's F-12 with 10% FBS.
3. Culture conditions are the same as those described previously in parts 3(a) and 3(b) of Example 9.
4. Methodology is the same as that described previously in part 4 of Example 9, except that, with reference to part 4 (b), cell concentration is adjusted to 1,000 cells per 100 µL (rather than 5,000 cells per 100 µL), and, with reference to part 4(e), test compounds are diluted in DMEM/F12 prior to addition to cell wells.
5. End point determination and data analysis are done as described previously in parts 5 and 6 of Example 9.
6. The results are presented in FIG. 3, which illustrates the marked inhibition of keratinocyte-proliferation, and consequently the marked anti-psoriatic activity, at concentrations above 10 µM of the compounds tested (CPR 3003 and CPR 3004).

EXAMPLE 11

Assay for Anti-inflammatory Activity by Inhibition of Macrophage Chemiluminescence The RAW 264.7 cell line (available from the ATCC under accession no. TIB 71) is a murine monocyte/macrophage line the cells of which show many of the differentiative functions of a macrophage. Like macrophages, the cells are capable of phagocytosis and undergo a respiratory burst (increased oxygen consumption) and production of oxygen radicals (e.g., superoxide) in response to appropriate activation signals. Agents that inhibit the activation of these cells in vitro, so as to inhibit the respiratory burst and corresponding production of oxygen radicals associated with the activation, are therefore inhibitors of macrophage activation and critical steps in inflammatory processes. These agents are likely, then, to be anti-inflammatories.

The respiratory burst and corresponding production of oxygen radicals that accompany macrophage activation can be measured in a variety of ways, including chemiluminescence based on the reaction of the oxygen radicals with luminol added to the culture medium (see M. A. Trush et al, 1978, "The Generation of Chemiluminescence by Phagocytic Cells," Methods in Enzymology 57: 462–494). Indeed, chemiluminescence generated from luminol in the culture medium of macrophage cell lines is recognized in the art as a marker of macrophage activation.

Figure 4:
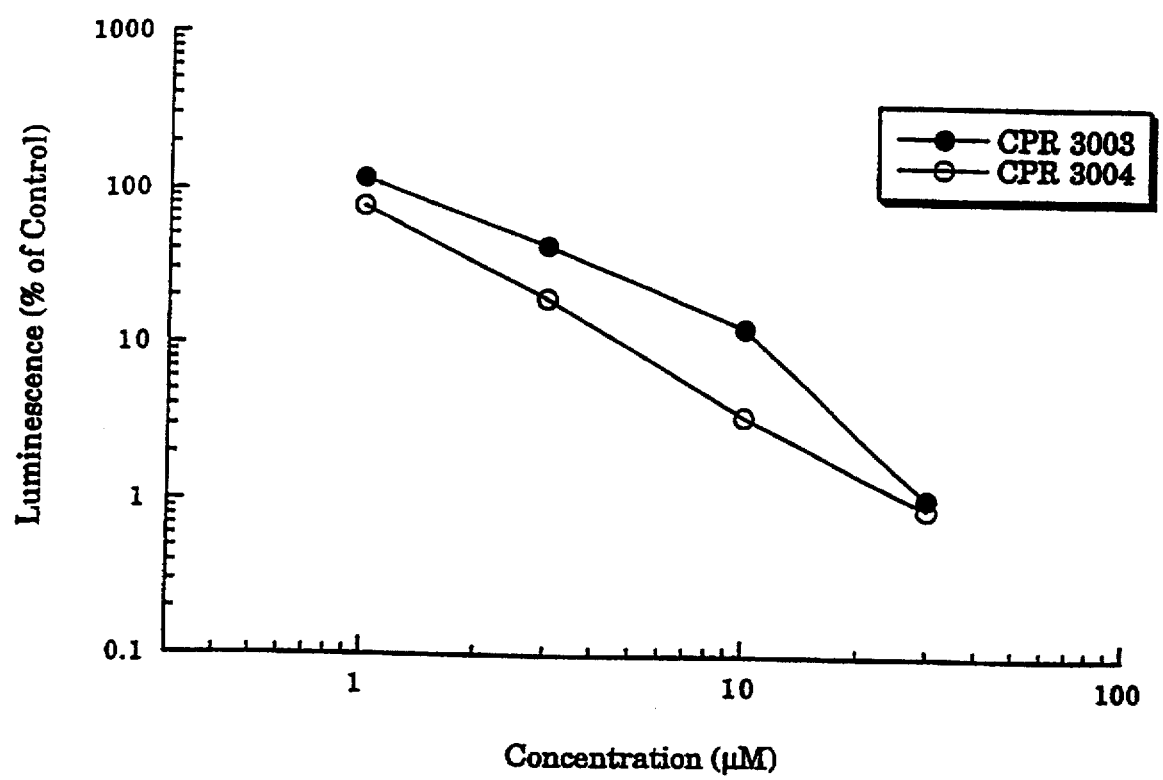
FIG. 4 is a graphical representation of results from an in vitro RAW 264.7 cell macrophage inhibition chemiluminescence assay of two compounds of the invention, designated CPR 3003 and CPR 3004.

1. Cell line: RAW 264.7 (ATCC TIB 71);
2. Culture medium: DMEM with 10% FBS (attachment dependent);
3. Standard protocol for culturing cell lines: in T-75 or T-150 flasks; 37° C.; 95% air, 5% $CO_2$; 100% humidity;
4. Cell lines are passaged when approximately 80% confluent with trypsin (1 mg/mL) and EDTA (1 mL EDTA in Ca-Mg free Hank's balanced salt solution), at a 1:4 to 1:5 split;
5. Trypsinize the cells and count with a hemocytometer;
6. Adjust concentration of cells to approximately 1,000,000 cells per mL;
7. Suspend cells in DMEM lacking phenol red and without FBS;
8. Pipette 1 mL, into a standard luminometer cuvet (12×75), commercially available from Analytical Luminescence Laboratories (San Diego, Calif.);
9. Add luminol to final concentration of 1 µM;
10. Add test compound at concentrations of 0, 1, 3, 10, or 30 µM;
11. Add 100 nanograms of phorbol myristate acetate (PMA);
12. Wait 1 minute and read photo counts (i.e., luminescence) on a Monolight 2010 luminometer available from Analytical Luminescence Laboratories;
13. The results are represented in FIG. 4, which illustrates the marked decrease in measured luminescence by the compounds tested at concentrations above 1 µM. Results are calculated as percent of control (no test compound present);
14. The results are also presented in Table 1, which tabulates the measured luminescence units at the indicated concentration of tested compound.

TABLE 1

| Concentration (µM)/Compound→ ↓ | CPR 3003 | CPR 3004 |
|---|---|---|
| | (Luminescence Units) | |
| 0 | 1,707,501 | 669,416 |
| 1 | 2,051,640 | 524,414 |
| 3 | 755,617 | 134,836 |
| 10 | 224,213 | 23,849 |
| 30 | 18,228 | 6,128 |

EXAMPLE 12

Assay for Anti-PAF Activity in Anesthetized Guinea Pigs

Guinea pigs of 650–1000 g were used in order to facilitate catheterization of the jugular vein and carotid artery. The guinea pigs were anesthetized with 35–45 mg/kg pentobarbital sodium. When or if the recordings described below were unstable, anesthetic additions were made during the course of the intervention. The cutdown was a ventral medial incision over the cervical area so that the trachea, jugular vein and carotid artery could be cannulated. The animals were immediately attached to a volume regulated Harvard® rodent respirator, Model 683, via a tracheostomy and the respirator was set at 60 respirations per minute and a volume of 8 ml/kg to maintain a normal arterial $P_{CO2}$ of approximately 40 mm Hg. Pancuronium bromide, a muscle relaxant, was then given intravenously at a dose of 0.2 mg/kg to prevent spontaneous breathing. A tube was connected to the respirator pump and the endotracheal catheter was attached to a pressure-transducing strain gauge and then to a 2-channel Gilson® physiological recorder. One channel of the recorder inscribed the pressure tracing from the airway; the second channel inscribed the pressure tracing from a similar strain gauge attached directly to a catheter inserted into the carotid artery. These two parameters were measured before and after each drug was given and at each increment in the dose response studies with each drug candidate and recorded. Total pulmonary resistance (TPR) was calculated as the difference between the expiratory pressure and inspiratory pressures with a constant volume.

After the anesthetic and muscle relaxant were given, the animal was allowed to stabilize. The airway was gently suctioned with a syringe and the lungs are briefly inflated by closing the expiratory port on the ventilator until the pressure was approximately three times resting pressure. When the pressure returned to a steady state, this TPR was considered control pressure. The dose-related increases or decreases were quantitated against these controls to determine the percent inhibition of PAF activity. Two doses of PAF were given as controls before the test compound was administered.

Figure 5:
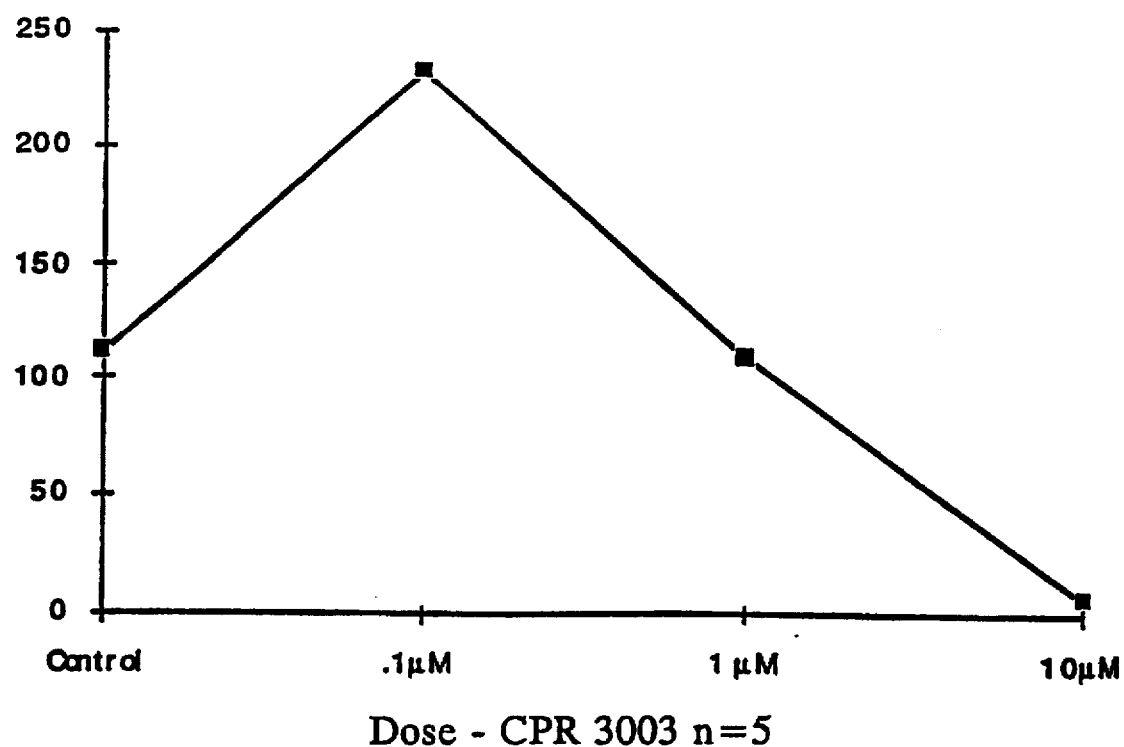
FIG. 5 is a graphical representation of results from an in vivo antagonism of PAF (Platelet Activating Factor)-induced increase in TPR (Total Pulmonary Resistance) by the compound of the invention, designated CPR 3003.

Incremental doses of 0.1, 1, and 10 µM of CPR 3003 change the PAF-induced increase in TPR in all animals as seen in Table 2 and in FIG. 5. Decreases of TPR in a dose-related way indicate an inhibition of the constrictor activity of PAF on the airway.

TABLE 2

| CPR 3003 n = 5 | % of Controls |
|---|---|
| PAF Control | 112.2 |
| .1 µM | 232.2 |
| 1 µM | 110 |
| 10 µM | 7 |

EXAMPLE 13

Tablets

This is an illustrative example of tablets containing the following ingredients which may be prepared in a conventional manner:

| Ingredient | Per Tablet (mg) |
|---|---|
| CPR-3003 | 50–100 |
| Lactose | 70 |
| Maize starch | 70 |
| Polyvinylpyrrolidone | 5 |
| Magnesium stearate | 5 |
| Tablet weight | 200–250 |

EXAMPLE 14

Oil-in-Water Cream Base Formulation

This is an illustrative example of oil-in-water cream base formulation for topical use that may be prepared in a conventional manner:

| Ingredient | Weight (g) |
|---|---|
| CPR-3004 | 10.0 |
| Anhydrous lanolin | 20.0 |
| Polysorbate 60 | 4.0 |
| Sorbitan monopalmitate | 2.0 |

-continued

| Ingredient | Weight (g) |
|---|---|
| Light liquid paraffin | 4.0 |
| Propylene glycol | 5.0 |
| Methyl hydroxybenzoate | 0.1 |
| Purified water | to 100.0 |

We claim:

1. An N-substituted glycerophosphoethanolamine of the formula:

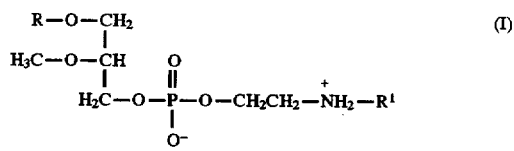

and the isomeric forms thereof; wherein R represents a substituted or unsubstituted straight or branched chain $C_{14-20}$ alkyl or alkenyl, said substituent being one or more of halo, $C_{1-3}$ alkoxy or cyano, provided that a double bond of said alkenyl does not involve the carbon atom of said alkenyl that is bonded to the oxygen of the glyceryl backbone; and $R^1$ is 3-(2-imidazolinyl)-2-imidazolinyl or 2-imidazolinyl; and the pharmaceutically acceptable salts thereof.

2. A compound of claim 1 wherein said R is $C_{16-18}$ alkyl and said $R^1$ is 3-(2-imidazolinyl)-2-imidazolinyl.

3. A compound of claim 1 wherein said R is $C_{16-18}$ alkyl and said $R^1$ is 2-imidazolinyl.

4. 1-O-n-Octadecyl-2-O-methyl-glycero-3-phospho-N-[3-(2-imidazolinyl)-2-imidazolinyl]-ethanolamine.

5. 1-O-n-Octadecyl-2-O-methyl-glycero-3-phospho-N-(2-imidazolinyl)-ethanolamine.

6. A method of treating a tumor in a mammal afflicted with same which comprises administering to said mammal an anti-tumor effective amount of an N-substituted glycerophosphoethanolamine of the formula:

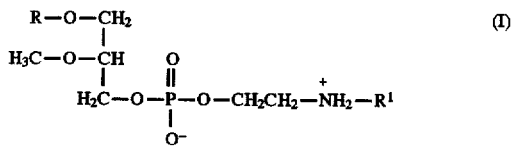

and the isomeric forms thereof; wherein R represents a substituted or unsubstituted straight or branched chain $C_{14-20}$ alkyl or alkenyl, said substituent being one or more of halo, $C_{1-3}$ alkoxy or cyano, provided that a double bond of said alkenyl does not involve the carbon atom of said alkenyl that is bonded to the oxygen of the glyceryl backbone; and $R^1$ is 3-(2-imidazolinyl)-2-imidazolinyl or 2-imidazolinyl; and the pharmaceutically acceptable salts thereof.

7. The method of claim 6 wherein said R is $C_{16-18}$ alkyl and said $R^1$ is 3-(2-imidazolinyl)-2-imidazolinyl.

8. The method of claim 6 wherein said R is $C_{16-18}$ alkyl and said $R^1$ is 2-imidazolinyl.

9. The method of claim 6 wherein the compound of formula (I) is 1-O-n-octadecyl-2-O-methyl-glycero-3-phospho-N-[3-(2-imidazolinyl)-2-imidazolinyl]-ethanolamine.

10. The method of claim 6 wherein the compound of formula (I) is 1-O-n-octadecyl-2-O-methyl-glycero-3-phospho-N-(2-imidazolinyl)-ethanolamine.

11. A method of treating psoriasis in a mammal afflicted with same which comprises administering to said mammal an anti-psoriatic effective amount of an N-substituted glycerophosphoethanolamine of the formula:

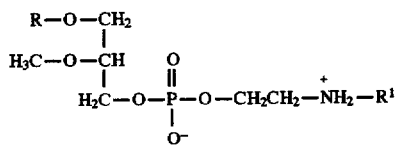

and the isomeric forms thereof; wherein R represents a substituted or unsubstituted straight or branched chain $C_{14-20}$ alkyl or alkenyl, said substituent being one or more of halo, $C_{1-3}$ alkoxy or cyano, provided that a double bond of said alkenyl does not involve the carbon atom of said alkenyl that is bonded to the oxygen of the glyceryl backbone; and $R^1$ is 3-(2-imidazolinyl)-2-imidazolinyl or 2-imidazolinyl; and the pharmaceutically acceptable salts thereof.

12. The method of claim 11 wherein said R is $C_{16-18}$ alkyl and said $R^1$ is 3-(2-imidazolinyl)-2-imidazolinyl.

13. The method of claim 11 wherein said R is $C_{16-18}$ alkyl and said $R^1$ is 2-imidazolinyl.

14. The method of claim 11 wherein the compound of formula (I) is 1-O-n-octadecyl-2-O-methyl-glycero-3-phospho-N-[3-(2-imidazolinyl)-2-imidazolinyl]-ethanolamine.

15. The method of claim 11 wherein the compound of formula (I) is 1-O-n-octadecyl-2-O-methyl-glycero-3-phospho-N-(2-imidazolinyl)-ethanolamine.

16. A method of treating inflammation in a mammal afflicted with same which comprises administering to said mammal an anti-inflammatory effective amount of an N-substituted glycerophosphoethanolamine of the formula:

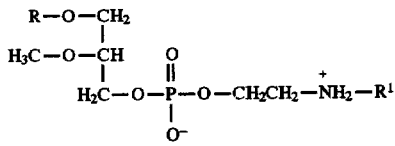

and the isomeric forms thereof; wherein R represents a substituted or unsubstituted straight or branched chain $C_{14-20}$ alkyl or alkenyl, said substituent being one or more of halo, $C_{1-3}$ alkoxy or cyano, provided that a double bond of said alkenyl does not involve the carbon atom of said alkenyl that is bonded to the oxygen of the glyceryl backbone; and $R^1$ is 3-(2-imidazolinyl)-2-imidazolinyl or 2-imidazolinyl; and the pharmaceutically acceptable salts thereof.

17. The method of claim 16 wherein said R is $C_{16-18}$ alkyl and said $R^1$ is 3-(2-imidazolinyl)-2-imidazolinyl.

18. The method of claim 16 wherein said R is $C_{16-18}$ alkyl and said $R^1$ is 2-imidazolinyl.

19. The method of claim 16 wherein the compound of formula (I) is 1-O-n-octadecyl-2-O-methyl-glycero-3-phospho-N-[3-(2-imidazolinyl)-2-imidazolinyl]-ethanolamine.

20. The method of claim 16 wherein the compound of formula (I) is 1-O-n-octadecyl-2-O-methyl-glycero-3-phospho-N-(2-imidazolinyl)-ethanolamine.

21. A pharmaceutical composition comprising an anti-tumor, anti-psoriatic or anti-inflammatory effective amount of an N-substituted glycerophosphoethanolamine of the formula:

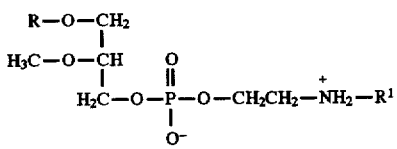

and the isomeric forms thereof; wherein R represents a substituted or unsubstituted straight or branched chain $C_{14-20}$ alkyl or alkenyl, said substituent being one or more of halo, $C_{1-3}$ alkoxy or cyano, provided that a double bond of said alkenyl does not involve the carbon atom of said alkenyl that is bonded to the oxygen of the glyceryl backbone; and $R^1$ is 3-(2-imidazolinyl)-2-imidazolinyl or 2-imidazolinyl; and the pharmaceutically acceptable salts thereof; and a pharmaceutically acceptable carrier.

22. The composition of claim 21 wherein said R is $C_{16-18}$ alkyl and said $R^1$ is 3-(2-imidazolinyl)-2-imidazolinyl.

23. The composition of claim 21 wherein said R is $C_{16-18}$ alkyl and said $R^1$ is 2-imidazolinyl.

24. The composition of claim 21 wherein the compound of formula (I) is 1-O-n-octadecyl-2-O-methyl-glycero-3-phospho-N-[3-(2-imidazolinyl)-2-imidazolinyl]-ethanolamine.

25. The composition of claim 21 wherein the compound of formula (I) is 1-O-n-octadecyl-2-O-methyl-glycero-3-phospho-N-(2-imidazolinyl)-ethanolamine.

26. A pharmaceutical composition for topical use comprising from about 0.1 to about 5.0 weight percent of a compound of claim 1 and a pharmaceutically acceptable carrier in ointment form.

27. The topical composition of claim 26 wherein said compound of formula (I) said R is $C_{16-18}$ alkyl and said $R^1$ is 3-(2-imidazolinyl)-2-imidazolinyl.

28. The topical composition of claim 26 wherein said compound of formula (I) said R is $C_{16-18}$ alkyl and said $R^1$ is 2-imidazolinyl.

29. The topical composition of claim 26 wherein said compound of formula (I) is 1-O-n-octadecyl-2-O-methyl-glycero-3-phospho-N-[3-(2-imidazolinyl)-2-imidazolinyl]-ethanolamine.

30. The topical composition of claim 26 wherein said compound of formula (I) is 1-O-n-octadecyl-2-O-methyl-glycero-3-phospho-N-(2 imidazolinyl)-ethanolamine.

* * * * *